(12) United States Patent
Ohto et al.

(10) Patent No.: US 6,316,216 B1
(45) Date of Patent: *Nov. 13, 2001

(54) MUTATED PRENYL DIPHOSPHATE SYNTHASES

(75) Inventors: Chikara Ohto; Hiroyuki Nakane, both of Toyota; Tokuzo Nishino, Sendai; Shinichi Ohnuma, Sendai; Kazutake Hirooka, Sendai, all of (JP)

(73) Assignee: Toyota Jidosha Kabushiki Kaisha, Toyota (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,126
(22) PCT Filed: Oct. 29, 1997
(86) PCT No.: PCT/JP97/03921
§ 371 Date: Apr. 27, 1999
§ 102(e) Date: Apr. 27, 1999
(87) PCT Pub. No.: WO98/20138
PCT Pub. Date: May 14, 1998

(30) Foreign Application Priority Data

Nov. 5, 1996 (JP) .................................... 8-307506

(51) Int. Cl.[7] .............. C12P 23/00; C12N 9/00; C12N 9/10; C12N 1/20; C12N 15/00
(52) U.S. Cl. ............. 435/67; 435/183; 435/252.3; 435/254.3; 435/320.1; 435/325; 435/193; 536/23.2
(58) Field of Search .............. 435/67, 193, 172.1, 435/252.3, 254.11, 325, 320.1; 536/23.2

(56) References Cited

U.S. PATENT DOCUMENTS 5,807,725 * 9/1998 Ohto et al. .................... 435/193

FOREIGN PATENT DOCUMENTS 0 537 553  4/1993  (EP).
0 674 000  9/1995  (EP).
0 733 709  9/1996  (EP).

OTHER PUBLICATIONS

Ohnuma et al. Conversion from farnesyl diphosphate synthase to geranylgeranyl diphosphate synthase by random chemical mutagenesis. Journal of Biological Chemistry. Apr. 26, 1996. vol. 271:10087–95.*

Ohnuma et al. A role of the amino acid residue located on the fifth position before the first aspartate–rich motif of farnesyl diphosphate synthase on determination of the final product. Journal of Biological Chemistry. Nov. 29, 1996. vol. 271:30748–54.*

Ohnuma S.–I.: "Conversion of Product Specificity of Archaebacterial Geranylgeranyl–Diphosphate Synthases" Journal of Biological Chemistry, vol. 271, No. 31, Aug. 2, 1996, pp. 18831–18837.

Marrero P.F. et a.: "Effects of Site–Directed Mutagenesis of the Highly Conserved Aspartate Residues in Domain II of Farnesyl Diphosphate Synthase Activity" Journal of Biological Chemistry, vol. 267, No. 30, Oct. 25, 1992, pp. 21873–21878.

* cited by examiner

Primary Examiner—Rebecca E. Prouty
Assistant Examiner—Manjunath N. Rao
(74) Attorney, Agent, or Firm—Kenyon & Kenyon

(57) ABSTRACT

A mutant prenyl diphosphate synthase having a modified amino acid sequence of prenyl diphosphate synthase, wherein the amino acid residue located at the eighth position in the N-terminal direction from D of the N-terminal of the Asp-rich domain DDXX(XX)D (in the sequence X denotes any amino acid and the two X's in the parentheses may not be present) present in the region II has been substituted by another amino acid, or both of the amino acid residue located at the fifth position in the N-terminal direction from D of the N-terminal and the amino acid residue located at the eighth position in the N-terminal direction from D of the N-terminal have been substituted by other amino acids.

20 Claims, 3 Drawing Sheets

Fig. 1

|  | REGION I | REGION II | | REGION III |
|---|---|---|---|---|
| ATGERPYRS | 116 GGKRVR | 147 EMIHTMSLIHDDLPCMDNDDLRRG | 238 | GQVVD |
| LA15778.p | 110 ...... | 141 ......................... | 230 | ..... |
| CAGERDIS. | 118 ...... | 149 ......................... | 238 | ..A.. |
| ATGGPSRP. | 88 .P..AP | 119 .V.AA...........D.PV.... | 211 | ..Y.. |
| GGPS.pep  | 43 ...L.. | 74 .VL..FT.V......I..Q.NI... | 160 | ..A.. |
| SPCRT.pep | 64 .A.I.. | 95 .L..CA..V.......F.DAEI... | 185 | .GME. |
| RCPHSYNG. | 192 .A.I.. | 223 .LM.CA..V.......AF..A.I.. | 313 | .AWE. |
| EHCRTS.pe | 54 ...... | 86 .LT..A..ML......M...AE... | 175 | .FR.. |
| MXCRTNODA | 104 ..L... | 136 .LL..FL.........VA.QAE... | 199 | .YL.. |
| NCAL3.pep | 197 ..DI.. | 226 ..L..A..LV.......VE..SV.. | 260 | .GM.. |
| BSFDPS.pe | 45 ...I.. | 76 ..Y...........S.......... | 159 | .AA.. |

|  | REGION IV | REGION V |
|---|---|---|
| ATGERPYRS | 265 KT | 293 GLLFQVVDDIL_DVTKSSK_ELGKTAGKDLIADK |
| LA15778.p | 255 .. | 283 ..M................V............ |
| CAGERDIS. | 263 .. | 291 ...................VV........... |
| ATGGPSRP. | 230 .F | 256 ..M.Y...........E................ |
| GGPS.pep  | 185 .. | 211 ..IA....I......TE..KK..YDGGAE.GMMEMAEEL. |
| SPCRT.pep | 203 .. | 227 ..EA....A...LR..ALCDAE_T....PVFS.IREG. |
| RCPHSYNG. | 331 .. | 355 ..SA...IA...LK..ALM.AE.AM..P..Q.IANER |
| EHCRTS.pe | 199 .. | 225 ..QA...LL...LRD.HPET.......DRN..A__G. |
| MXCRTNODA | 226 .. | 247 ..AY.LR.L.GLFGD.NV___A..A.DG.FLQG. |
| NCAL3.pep | 286 .. | 272 ..I...IA..YHNLWNREYT_AN.GMCE..TEG. |
| BSFDPS.pe | 183 .. | 218 ..A...IL......___IEGAEE_KI.PV.S.QSNN. |

SEQUENCE LISTING

<160> NUMBER OF SEQ ID NOS: 15

<210> SEQ ID NO 1
<211> LENGTH: 330
<212> TYPE: PRT
<213> ORGANISM: Sulfolobus acidocaldarius
<220> FEATURE:
<223> OTHER INFORMATION: 82-86 is an Asp-rich domain

<400> SEQUENCE: 1

```
Met Ser Tyr Phe Asp Asn Tyr Phe Asn Glu Ile Val Asn Ser Val Asn
  1               5                  10                  15

Asp Ile Ile Lys Ser Tyr Ile Ser Gly Asp Val Pro Lys Leu Tyr Glu
             20                  25                  30

Ala Ser Tyr His Leu Phe Thr Ser Gly Gly Lys Arg Leu Arg Pro Leu
         35                  40                  45

Ile Leu Thr Ile Ser Ser Asp Leu Phe Gly Gly Gln Arg Gly Arg Ala
     50                  55                  60

Tyr Tyr Ala Gly Ala Ala Ile Glu Val Leu His Thr Phe Thr Leu Val
 65                  70                  75                  80

His Asp Asp Ile Met Asp Gln Asp Asn Ile Arg Arg Gly Leu Pro Thr
                 85                  90                  95

Val His Val Lys Tyr Gly Leu Pro Leu Ala Ile Leu Ala Gly Asp Leu
            100                 105                 110
```

```
Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Arg Lys
                325                 330

<210> SEQ ID NO 2
<211> LENGTH: 993
<212> TYPE: DNA
<213> ORGANISM: Sulfolobus acidocaldarius
<220> FEATURE:
<223> OTHER INFORMATION: 246-258 is an Asp-rich coding domain

<400> SEQUENCE: 2
atgagttact tgacaacta ttttaatgag attgttaatt ctgtaaacga cattattaag      60
agctatatat ctggagatgt tcctaaacta tatgaagcct catatcattt gtttacatct    120
ggaggtaaga ggttaagacc attaatctta actatatcat cagatttatt cggaggacag    180
agagaaagag cttattatgc aggtgcagct attgaagttc ttcatacttt tacgcttgtg    240
catgatgata ttatggatca agataatatc agaagagggt tacccacagt ccacgtgaaa    300
tacggcttac ccttagcaat attagctggg gatttactac atgcaaaggc ttttcagctc    360
ttaacccagg ctcttagagg tttgccaagt gaaaccataa ttaaggcttt cgatattttc    420
actcgttcaa taataattat atccgaagga caggcagtag atatggaatt tgaggacaga    480
attgatataa aggagcagga ataccttgac atgatctcac gtaagacagc tgcattattc    540
tcggcatcct caagtatagg cgcacttatt gctggtgcta atgataatga tgtaagactg    600
atgtctgatt tcggtacgaa tctaggtatt gcatttcaga ttgttgacga tatcttaggt    660
ctaacagcag acgaaaagga acttggaaag cctgttttta gtgatattag ggagggtaaa    720
aagactatac ttgtaataaa aacactggag ctttgtaaag aggacgagaa gaagattgtc    780
ctaaaggcgt taggtaataa gtcagcctca aaagaagaat taatgagctc agcagatata    840
```

```
attaagaaat actctttaga ttatgcatac aatttagcag agaaatatta taaaaatgct      900
atagactctt taaatcaagt ctcctctaag agtgatatac ctggaaaggc tttaaaatat      960
ctagctgaat ttacgataag aaggagaaaa taa                                   993
```

<210> SEQ ID NO 3
<211> LENGTH: 297
<212> TYPE: PRT
<213> ORGANISM: Bacillus stearothermophilus
<220> FEATURE:
<223> OTHER INFORMATION: 86-92 is an Asp-rich domain

<400> SEQUENCE: 3

```
Met Ala Gln Leu Ser Val Glu Gln Phe Leu Asn Glu Gln Lys Gln Ala
 1               5                  10                  15

Val Glu Thr Ala Leu Ser Arg Tyr Ile Glu Arg Leu Glu Gly Pro Ala
            20                  25                  30

Lys Leu Lys Lys Ala Met Ala Tyr Ser Leu Glu Ala Gly Gly Lys Arg
        35                  40                  45

Ile Arg Pro Leu Leu Leu Ser Thr Val Arg Ala Leu Gly Lys Asp
    50                  55                  60

Pro Ala Val Gly Leu Pro Val Ala Cys Ala Ile Glu Met Ile His Thr
65                  70                  75                  80

Tyr Ser Leu Ile His Asp Asp Leu Pro Ser Met Asp Asn Asp Asp Leu
                85                  90                  95

Arg Arg Gly Lys Pro Thr Asn His Lys Val Phe Gly Glu Ala Met Ala
            100                 105                 110

Ile Leu Ala Gly Asp Gly Leu Leu Thr Tyr Ala Phe Gln Leu Ile Thr
        115                 120                 125

Glu Ile Asp Asp Glu Arg Ile Pro Pro Ser Val Arg Leu Arg Leu Ile
    130                 135                 140

Glu Arg Leu Ala Lys Ala Ala Gly Pro Glu Gly Met Val Ala Gly Gln
145                 150                 155                 160

Ala Ala Asp Met Glu Gly Glu Gly Lys Thr Leu Thr Leu Ser Glu Leu
                165                 170                 175

Glu Tyr Ile His Arg His Lys Thr Gly Lys Met Leu Gln Tyr Ser Val
            180                 185                 190

His Ala Gly Ala Leu Ile Gly Gly Ala Asp Ala Arg Gln Thr Arg Glu
        195                 200                 205

Leu Asp Glu Phe Ala Ala His Leu Gly Leu Ala Phe Gln Ile Arg Asp
    210                 215                 220

Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
                245                 250                 255

Leu Ala Gly Ala Lys Glu Lys Leu Ala Phe His Ile Glu Ala Ala Gln
            260                 265                 270

Arg His Leu Arg Asn Ala Asp Val Asp Gly Ala Ala Leu Ala Tyr Ile
        275                 280                 285

Cys Glu Leu Val Ala Ala Arg Asp His
    290                 295
```

<210> SEQ ID NO 4
<211> LENGTH: 894
<212> TYPE: DNA
<213> ORGANISM: Bacillus stearothermophilus

```
<220> FEATURE:
<223> OTHER INFORMATION: 256-276 is an Asp-rich coding domain

<400> SEQUENCE: 4
gtggcgcagc tttcagttga acagtttctc aacgagcaaa acaggcggt ggaaacagcg      60 ctctcccgtt atatagagcg cttagaaggg ccggcgaagc tgaaaaaggc gatggcgtac    120
tcattggagg ccggcggcaa acgaatccgt ccgttgctgc ttctgtccac cgttcgggcg    180
ctcggcaaag acccggcggt cggattgccc gtcgcctgcg cgattgaaat gatccatacg    240
tactctttga tccatgatga tttgccgagc atggacaaca tgatttgcg gcgcggcaag    300 ccgacgaacc ataaagtgtt cggcgaggcg atggccatct tggcggggga cgggttgttg    360
acgtacgcgt ttcaattgat caccgaaatc gacgatgagc gcatccctcc ttccgtccgg    420
cttcggctca tcgaacggct ggcgaaagcg gccggtccgg aagggatggt cgccggtcag    480
gcagccgata tggaaggaga ggggaaaacg ctgacgcttt cggagctcga atacattcat    540
cggcataaaa ccgggaaaat gctgcaatac agcgtgcacg ccggcgcctt gatcggcggc    600
gctgatgccc ggcaaacgcg ggagcttgac gaattcgccg cccatctagg ccttgccttt    660
caaattcgcg atgatattct cgatattgaa ggggcagaag aaaaaatcgg caagccggtc    720
ggcagcgacc aaagcaacaa caaagcgacg tatccagcgt tgctgtcgct tgccggcgcg    780
aaggaaaagt tggcgttcca tatcgaggcg gcgcagcgcc atttacggaa cgccgacgtt    840
gacggcgccg cgctcgccta tatttgcgaa ctggtcgccg cccgcgacca ttaa          894

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
ggtgcagcaa ttgaagttgg tcatact                                          27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
catactgcta cgcttgttca tgatg                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
catactggta cgcttgttca tgatg                                            25

<210> SEQ ID NO 8
<211> LENGTH: 20
<212> TYPE: DNA
<213> ORGANISM: Artificial Sequence
```

```
<220> FEATURE:
<223> OTHER INFORMATION: Description of Artificial Sequence: synthetic
      DNA

<400> SEQUENCE: 8
aaacagacca tggcgctttc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
cagccaagct tttaatggtc                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
ctttgattca tgatgatttg                                                    20

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
atcatcatga atcaaagaag acgtatggcc catttc                                  36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
atcatcatga atcaaagagg ccgtatggcc catttc                                  36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
atcatcatga atcaaagagc ccgtatggcc catttc                                  36

<210> SEQ ID NO 14
<211> LENGTH: 20
<212> TYPE: DNA
<213> ORGANISM: Artificial Sequence
<220> FEATURE:
```

-continued

```
<223> OTHER INFORMATION: Description of Artificial Sequence: synthetic
      DNA

<400> SEQUENCE: 14
atggacaacg atgatttgcg                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
caaatcatca tggatcaaag                                                   20
```

MUTATED PRENYL DIPHOSPHATE SYNTHASES

TECHNICAL FIELD

The present invention relates to novel mutant enzymes which synthesize linear prenyl diphosphates that are precursors of compounds important for organisms, such as steroids, ubiquinones, dolichols, carotenoids, prenylated proteins, animal hormones, plant hormones and the like, and to a gene and production of the enzymes.

BACKGROUND ART

Many substances having important functions in organisms are biosynthesized using isoprene (2-methyl-1,3-butadiene) as a building block. These compounds are also called isoprenoids, terpenoids, or terpenes, and are classified depending on the number of carbon atoms into hemiterpenes (C5), monoterpenes (C10), sesquiterpenes (C15), diterpenes (C20), sesterterpenes (C25), triterpenes (C30), tetraterpenes (C40) and the like. The biosynthesis starts with the mevalonate pathway through which mevalonic acid-5-diphosphate is synthesized, followed by the synthesis of isopentenyl diphosphate (IPP) which is an active isoprene unit.

The true entity of the isoprene unit that was proposed as a putative precursor was found to be isopentenyl diphosphate, the so-called active-form isoprene unit. While dimethylallyl diphosphate (DMAPP), an isomer of isopentenyl diphosphate, is used as a substrate in the reaction of isopentenyl adenine which is known as a cytokinin of plant hormones, it is also known to undergo a condensation reaction with isopentenyl diphosphate to synthesize linear active isoprenoids such as geranyl diphosphate (GPP), neryl diphosphate, farnesyl diphosphate (FPP), geranylgeranyl diphosphate (GGPP), geranylfarnesyl diphosphate (GFPP), hexaprenyl diphosphate (HexPP), heptaprenyl diphosphate (HepPP) and the like. There are the Z type and the E type in the condensation reaction. Geranyl diphosphate is a product of the E type condensation and neryl diphosphate of the Z type condensation.

Although, the all-E type is considered to be the active form in farnesyl diphosphate and geranylgeranyl diphosphate, the Z type condensation reaction leads to the synthesis of various polyprenols found in natural rubber, dolichols, bactoprenols (undecaprenols), and plants. They are believed to undergo the condensation reaction using the phosphate ester bond energy of the pyrophosphate and the carbon backbone present in the molecule and to produce pyrophosphate as the byproduct of the reaction.

Farnesyl diphosphate or geranylgeranyl diphosphate serves as a reaction substrate leading to the synthesis of prenylated proteins (from farnesyl diphosphate or geranylgeranyl diphosphate) represented by the G protein that is important in the mechanism of signal transduction in the cell; cell membrane lipids (from geranylgeranyl diphosphate) of archaea; squalene (from farnesyl diphosphate) which is a precursor of steroids; and of phytoene (from geranylgeranyl diphosphate) which is a precursor of carotenoids. Prenyl diphosphates from hexaprenyl diphosphate and heptaprenyl diphosphate having six and seven isoprene units, respectively, to prenyl diphosphates having ten isoprene units serve as the precursors of synthesis of ubiquinone and menaquinone (vitamin K2) that work in the electron transport system.

Furthermore, via the biosynthesis of these active-form isoprenoids, a large number of compounds that are essential for the life are synthesized. Just to mention a few, there are plant hormones, cytokinins and isopentenyl adenosine-modified tRNA which use hemiterpenes as precursor for synthesis thereof, monoterpene geraniols and its isomer of nerol that are the main components of the rose oil perfume, and a camphor tree extract, camphor, which is an insecticide. Sesquiterpenes include juvenile hormones of insects, diterpenes include plant hormone gibberellins, trail pheromones of insects, and retinols and retinals that function as brown pigment precursors, binding components of the purple membrane proteins of extremely halophilic microorganisms, and vitamin A.

Furthermore, using squalene which is a triterpene, a vast variety of steroid compounds are synthesized, including, for example, animal sex hormones, vitamin D, ecdysone which is an ecdysis hormone of insects, a plant hormone brassinolide, the components of plasma membrane. Various carotenoids of tetraterpenes that are precursors of various pigments of organisms and vitamin A are also important compounds derived from active isoprenoids. Compounds such as chlorophyll, pheophytin, tocopherol (vitamin E), and phylloquinone (vitamin K1) are also derived from tetraterpenes.

The active isoprenoid synthases that consecutively condense isopentenyl diphosphates with such allylic substrates as dimethylallyl diphosphate, geranyl diphosphate, farnesyl diphosphate, geranylgeranyl diphosphate, geranylfarnesyl diphosphate, etc. are called the prenyl diphosphate synthases, and are also called, based on the name of the compound having the maximum chain length of the major reaction products, for example farnesyl diphosphate synthase (FPP synthase), geranylgeranyl diphosphate (GGPP synthase) and the like.

So far there have been reports on purification, activity measurement, gene cloning, and sequencing of the nucleotide sequences of the genes of enzymes such as farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase (solanesyl diphosphate synthase), undecaprenyl diphosphate synthase and the like from bacteria, archaea, fungi, plants, and animals.

These active isoprenoid synthases constituting the basis of synthesis of a great variety of compounds that are important both in the industry and in the academic field of life sciences have few practical uses in industrial applications due to their unstable nature and low specific activities. However, with the isolation of thermostable prenyl diphosphate synthases from thermophilic bacteria and archaea and the genes encoding these enzymes, their availability as the enzymes is increased.

With regard to farnesyl diphosphate synthase, a gene was isolated from a moderate thermophile, *Bacillus stearothermophilus,* and an enzyme having a moderate thermostability was prepared using *Escherichia coli* as the host cell [T. Koyama et al. (1993) J. Biochem., 113: 355–363; Japanese Unexamined Patent Publication No. 5(1993)-219961]. With regard to geranylgeranyl diphosphate synthase, a gene was isolated from an extreme thermophile such as *Sulfolobus acidocaldarius* and *Thermus thermophilus* [S. -i. Ohnuma et al., (1994) J. Biol. Chem., 269: 14792–14797; Japanese Unexamined Patent Publication No. 7(1995)-308193, and; Japanese Unexamined Patent Application No. 7(1995)-294956], and enzymes having an extreme thermostability were prepared.

Furthermore, with regard to the prenyl diphosphate synthase having the functions of both of the farnesyl diphosphate synthase and the geranylgeranyl diphosphate synthase, the enzyme and the gene encoding it have been isolated from extremely thermophilic *Methanobacterium thermoautotrophicum* [A. Chen and D. Poulter (1993) J. Biol. Chem., 268: 11002–11007; A. Chen and D. Poulter (1994) ARCHIVES OF BIOCHEMISTRY AND BIOPHYSICS 314], and the thermostability of the enzyme has been demonstrated.

The enzymes that synthesize prenyl diphosphates having up to 20 carbons are homodimers, which relatively easily react in vitro and on which there have been many reports. However, it is believed that the enzymes that synthesize prenyl diphosphates having a longer chain length are heterodimers or that the enzymes may require other factors such as lipids, and hence for their industrial application to be effected it was necessary, and difficult, to find conditions that enable reorganization of the two subunits or other factors.

Thus, a technology has been desired that enables production of the thermostable and homodimer-type prenyl diphosphate synthases capable of synthesizing prenyl diphosphates having a longer chain length by artificially modifying amino acid sequences of the thermostable homodimer-type prenyl diphosphate synthases derived from thermophilic organisms.

With regard to the prenyl diphosphate synthases derived from thermophilic organisms, there are reports on the modification of FPP synthase derived from *Bacillus stearothermophilus* and GGPP synthase derived from *Sulfolobus acidocaldarius*.

The mutant type of FPP synthase derived from *Bacillus stearothermophilus* was selected based on the color change of the cell caused by lycopene that was produced by coexistence in *Escherichia coli* of crtB (the gene of phytoene synthase) and CrtI (the gene of the phytoene unsaturase and cis:trans isomerase derived from *Erwinia uredovora* and the gene of mutant FPP synthase derived from *Bacillus stearothermophilus* [Japanese patent application No. 7(1995)-25253].

Furthermore, the mutant enzyme of GGPP synthase and its gene derived from *Sulfolobus acidocaldarius* were selected based on the ability of complementing the glycerol metabolism of the HexPP synthase-deficient mutant *Saccharomyces cereviceae* [Japanese patent application No. 7(1995)-247043].

From the information of the gene of GGPP synthase of the mutant *Sulfolobus acidocaldarius*, it has been found that of the two Asp-rich domains that have been proposed based on the analysis of the amino acid sequences of the prenyl diphosphate synthases, the amino acid residue located at the fifth position in the N-terminal direction from D of the N-terminal of the Asp-rich conserved sequence I $D_1D_2X_1(X_2X_3)X_4D_3$ is responsible for controlling the chain length of the reaction product. Hence, a method has been invented that controls the reaction product for the purpose of increasing the chain length of the reaction product [a Japanese patent application filed on Jul. 3, 1996 under the title of "A Mutant Prenyl Diphosphate Synthase"]. The enzymes produced by using the method enables production of several reaction products that have a longer chain length than the corresponding native prenyl diphosphate synthase. However, even in these mutant prenyl diphosphate synthases, the change in chain length of reaction products is up to the level of hexaprenyl diphosphate at most, and methods have not been not known that enables production of prenyl diphosphates having a longer chain length.

SUMMARY OF INVENTION

It is an object of the invention to establish a method for producing long chain-prenyl diphosphate synthases by modifying amino acid residues of prenyl diphosphate synthases. Once a new enzyme having a property that is more adaptable to industrial application such as higher stability, higher specific activity, etc. has been obtained, it is possible, by modifying amino acid residues of the enzyme, to obtain immediately mutant prenyl diphosphate synthases and the genes therefor, that produce long chain-prenyl diphosphates and that retain the property of the corresponding native prenyl diphosphate synthase.

From the information on the nucleotide sequence of the mutant gene of the geranylgeranyl diphosphate synthase of the *Sulfolobus acidocaldarius*. It was found that of the two Asp-rich domains that have been proposed based on the analysis of the amino acid sequences of prenyl diphosphate synthases, the amino acid located at the fifth position in the N-terminal direction and the amino acid residue located at the eighth position in the N-terminal direction from the D of the N-terminal of the Asp-rich domain I $D_1D_2X_1(X_2X_3)X_4D_3$ are involved in the control of chain length of the reaction products.

Thus, the present invention provides a mutant prenyl diphosphate synthase having a modified amino acid sequence of prenyl diphosphate synthase, wherein the amino acid residue located at the eighth position in the N-terminal direction from D of the N-terminal of the Asp-rich domain $D_1D_2X_1(X_2X_3)X_4D_3$ (in the sequence X denotes any amino acid and the two X's in the parentheses may not be present) present in the region II has been substituted by another amino acid, or both of the amino acid residue located at the fifth position in the N-terminal direction from D of the N-terminal and the amino acid residue located at the eighth position in the N-terminal direction from D of the N-terminal have been substituted by other amino acids. The present invention further provides a mutant prenyl diphosphate synthase having a further modified amino acid sequence wherein the amino acid located at the second position in the N-terminal direction and/or the amino acid located at the third position in the N-terminal direction from D of the C-terminal side of said Asp-rich domain DDXXXXD have been deleted.

The present invention provides a mutant prenyl diphosphate synthase that retains the property of the corresponding native prenyl diphosphate synthase and that produces prenyl diphosphate having not less than 20 carbons such as geranylgeranyl diphosphate, geranylfarnesyl diphosphate, hexaprenyl diphosphate, heptaprenyl diphosphate, octaprenyl diphosphate, nonaprenyl diphosphate, decaprenyl diphosphate, undecaprenyl diphosphate, dodecaprenyl diphosphate, tridecaprenyl diphosphate, tetradecaprenyl diphosphate, pentadecaprenyl diphosphate, hexadecaprenyl diphosphate and the like.

The present invention further provides a recombinant vector, specifically an expression vector, comprising the above DNA.

The present invention further provides a DNA or RNA encoding the above enzyme.

The present invention further provides a host transformed by the above vector.

The present invention further provides a process for producing prenyl diphosphates having not less than 20 carbons characterized in that the above enzyme is contacted with a substrate selected from the group consisting of isopentenyl diphosphate, dimethylallyl diphosphate, geranyl diphosphate, farnesyl diphosphate, and geranylgeranyl diphosphate.

The present invention further provides a process of production of the mutant enzyme, said method comprising the steps of culturing the above host and of harvesting the expression product from the culture.

BRIEF EXPLANATION OF THE DRAWINGS

FIG. 1 is an alignment showing the regions (I) to (V) and the Asp-rich domain I of various prenyl diphosphate synthases. In the figure, the sequence represents the amino acid sequence of prenyl diphosphate synthase, and ATGERPYRS is geranylgeranyl diphosphate synthase derived from *Arabidopsis thaliana*, LA15778.p from *Lupinas albus*, CAGERDIS. from *Capsicum annuum*, ATGGPSRP. from *Arabidopsis thaliana*, GGPS.pep from *Sulfolobus acidocaldarius*, SPCRT.pep from *Rhodobactor sphaeroides*, RCPHSYNG. from *Rhodobactor capsulatus*, EHCRTS.pe from *Erwinia herbicola*, MXCRTNODA from *Myxococcus thaliana*, NCAL3.pep from *Neurospora crassa*, and BSFDPS.pe is farnesyl diphosphate synthase derived from *Bacillus stearothermophilus*. The number indicated on the left of each amino acid sequence represents the number of the N-terminal position of each amino acid sequence counted from the N-terminal of each geranylgeranyl diphosphate synthase.

FOH is farnesol, and GGOH is geranyl geraniol, which are produced from dephosphorylation of farnesyl diphosphate and geranylgeranyl diphosphate, respectively. Furthermore, prenyl alcohol that was produced by dephosphorylation of a longer chain-prenyl diphosphate is observed.

Figure 3:
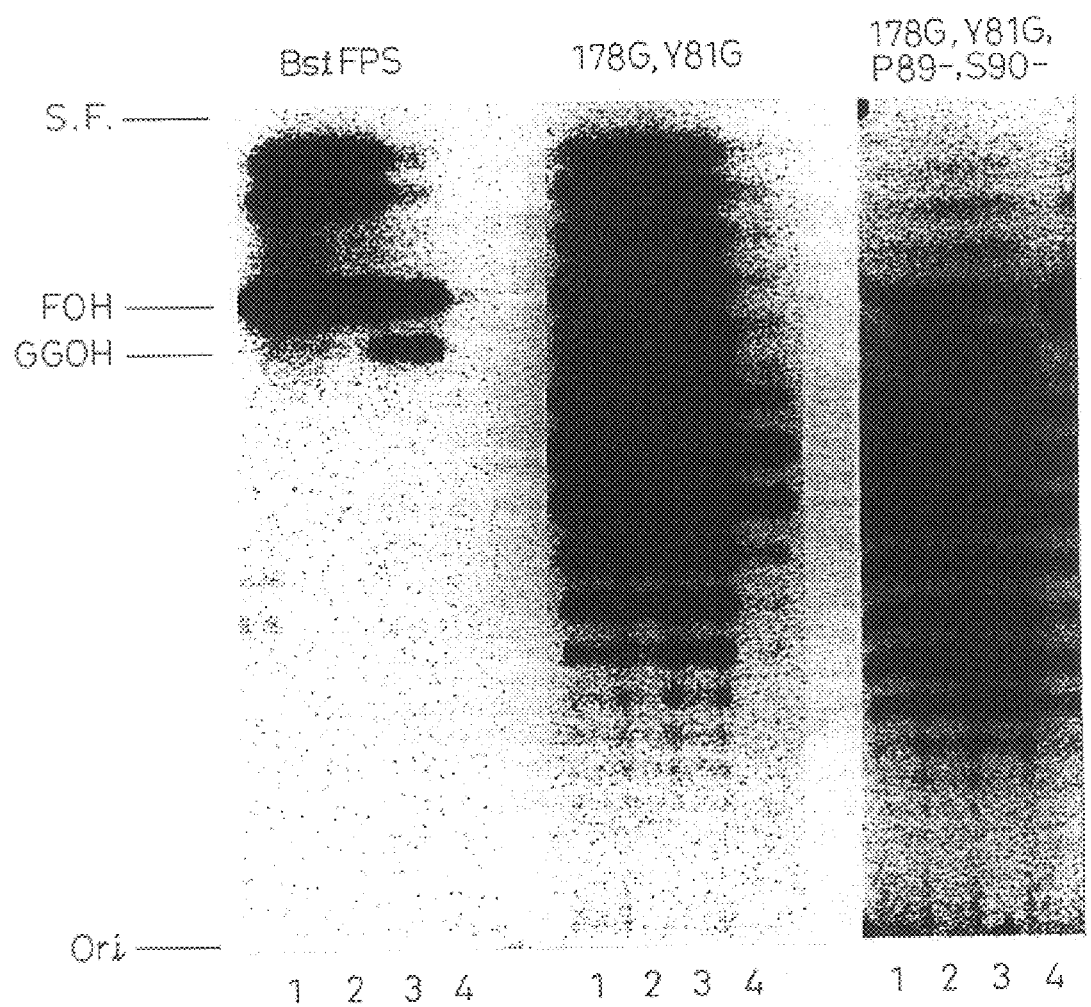

FIG. 3 shows a photograph of a profile of thin layer chromatography obtained on the dephosphorylated reaction products of the mutant BstFPS synthase when dimethyl allyl diphosphate, geranyl diphosphate, farnesyl diphosphate, and geranylgeranyl diphosphate were each used as the allylic substrate. In the figure, Ori. represents the origin of development, and S.F. represents the solvent front. Development has been conducted for each mutant BstFPS synthase. In the figure, BstFPS represents the wild type enzyme and the others represent the mutant enzymes. Lane numbers indicate the allylic primers (substrates) used in the reaction, and dimethylallyl diphosphate was used in lane 1; geranyl diphosphate in lane 2; farnesyl diphosphate in lane 3, and; geranylgeranyl diphosphate in lane 4.

FOH is farnesol, and GGOH is geranyl geraniol, which are produced from dephosphorylation of farnesyl diphosphate and geranylgeranyl diphosphate, respectively. Furthermore, prenyl alcohol that was produced by dephosphorylation of a longer chain-prenyl diphosphate is observed.

DETAILED DESCRIPTION

It has been proposed that there are five conserved regions in the amino acid sequence of a prenyl diphosphate synthase (one subunit in the case of a heterodimer) [A. Chen et al., Protein Science Vol. 3, pp. 600–607, 1994]. It is also known that of the five conserved regions, there is an Asp-rich domain conserved sequence I $D_1D_2X_1(X_2X_3)X_4D_3$ (the two X's in the parentheses may not be present) in region II. Although there is also an Asp-rich domain that is indicated as "DDXXD" in region V, the Asp-rich domain used to specify the modified region of the amino acid sequence of the present invention is the one present in region II, and this domain is termed as the Asp-rich domain I as compared to the Asp-rich domain II present in region V.

As the prenyl diphosphate synthases having the Asp-rich domain as described above, there can be mentioned farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase, undecaprenyl diphosphate synthase and the like.

More specific examples include the farnesyl diphosphate synthase of *Bacillus stearothermophilus*, the farnesyl diphosphate synthase of *Escherichia coli*, the farnesyl diphosphate synthase of *Saccharomyces cerevisiae*, the farnesyl diphosphate synthase of the rat, the farnesyl diphosphate synthase of the human, the geranylgeranyl diphosphate synthase of *Neurospora crassa*, the hexaprenyl diphosphate synthase of *Saccharomyces cerevisiae* and the like.

By way of example of some of these, the regions I to V of the amino acid sequences of prenyl diphosphate synthases, and the Asp-rich domain I (in the box) in the region II are shown in FIG. 1.

The present invention can be applied to any prenyl diphosphate synthase having the Asp-rich domain I.

In accordance with the present invention, there is provided a mutant prenyl diphosphate synthase having a modified amino acid sequence of prenyl diphosphate synthase, wherein the amino acid residue located at the eighth position in the N-terminal direction from D of the N-terminal of the Asp-rich domain $D_1D_2X_1(X_2X_3)X_4D_3$ (in the sequence X denotes any amino acid and the two X's in the parentheses may not be present) present in the region II has been substituted by another amino acid, or both of the amino acid residue located at the fifth position in the N-terminal direction from D of the N-terminal and the amino acid residue located at the eighth position in the N-terminal direction from D of the N-terminal have been substituted by other amino acids.

Furthermore, there is provided a mutant prenyl diphosphate synthase having a further modification of its amino acid sequence, wherein the amino acid residue located at the second position in the N-terminal direction and/or the amino acid located at the third position in the N-terminal direction from D of the C-terminal of the above Asp-rich domain DDXXXXD have been deleted.

The mutant prenyl diphosphate synthase of the present invention can synthesize a prenyl diphosphate having a longer chain length than the prenyl diphosphate synthesized by the corresponding native prenyl diphosphate synthase.

In accordance with the present invention, by way of example, the gene of the geranylgeranyl diphosphate synthase of an extremely thermophilic archaea, *Sulfolobus acidocaldarius*, is used as the starting material. *Sulfolobus acidocaldarius* is available from ATCC as ATCC No. 33909. The method for cloning the gene has been described in detail in Japanese Unexamined Patent Publication No. 6(1994)-315572. It has also been disclosed with the accession No. D28748 in a genetic information data base such as GenBank. By using the sequence it can be cloned by the conventional method known in the art. An example of the other cloning methods is illustrated in Example 1 herein and its nucleotide sequence is shown as SEQ ID No: 2.

In accordance with the present invention, by way of example, there are mentioned the enzymes having the amino acid sequences wherein which the following amino acids have been substituted in the amino acid sequence of the prenyl diphosphate synthase derived from *Sulfolobus acidocaldarius* as set forth in SEQ ID No: 1.

Mutant enzyme 1: Changes from Leu at position 74 to Gly, and Phe at position 77 to Ala;

Mutant enzyme 2: Changes from Leu at position 74 to Gly, and Phe at position 77 to Ser;

Mutant enzyme 3: Changes from Leu at position 74 to Gly, and Phe at position 77 to Gly.

In accordance with the present invention, by way of example, the gene of the farnesyl diphosphate synthase of a thermophilic bacterium, *Bacillus stearothermophilus*, is used as the starting material. *Bacillus stearothermophilus* is available from ATCC as ATCC No. 10149. The method for cloning the gene has been described in detail in Japanese Unexamined Patent Publication No. 5(1993)-219961. It has also been disclosed with the accession No. D13293 in a genetic information data base such as GenBank. By using the sequence it can be cloned in the conventional method known in the art. An example of the other cloning methods is illustrated in Example 2 herein and its nucleotide sequence is shown as SEQ ID No: 4.

In accordance with the present invention, by way of example, there are mentioned the enzymes having the amino acid sequences wherein the following amino acids have been substituted in the amino acid sequence of the prenyl diphosphate synthase derived from *Bacillus stearothermophilus* as set forth in SEQ ID No: 3:

Mutant enzyme 4: Changes from Ile at position 78 to Gly, and Tyr at position 81 to Gly;

Mutant enzyme 5: Changes from Ile at position 78 to Gly, and Tyr at position 81 to Gly, and deletion of Pro at position at 89 and Ser at position at 90.

Mutant enzyme 6: Changes from Ile at position 78 to Gly, and Tyr at position 81 to Ala;

Mutant enzyme 7: Changes from Ile at position 78 to Gly, and Tyr at position 81 to Ala, and deletion of Pro at position 89 and Ser at position 90;

Mutant enzyme 8: Changes from Ile at position 78 to Gly, and Tyr at position 81 to Ser;

Mutant enzyme 9: Changes from Ile at position 78 to Gly, and Tyr at position 81 to Ser, and deletion of Pro at position 89 and Ser at position 90.

It is known that an enzyme can sometimes exhibit its original enzymatic activity even when it has been modified by addition, removal, and/or replacement of one or a few amino acids as compared to the original amino acid sequence. Therefore, the present invention is intended to encompass those enzymes that have been modified by addition, deletion, and/or substitution of one or a few, for example up to five, or up to 10, amino acids as compared to the amino acid sequence as set forth in SEQ ID No: 1 or 3 of and that can still perform its original function.

The present invention further provides a protein encoded by a nucleic acid that hybridizes with, for example, a nucleic acid having a base sequence coding for a prenyl diphosphate synthase as set forth in SEQ ID No: 2 or 4 at under an ordinary condition such as a stringency condition of 6 to 0.2×SSC at 50 to 65° C., said protein having an activity of prenyl diphosphate synthase.

The present invention also provides the genes encoding various mutant enzymes mentioned above, the vectors containing these genes, specifically expression vectors, and the hosts transformed by said vectors. The gene (DNA) of the present invention can be readily obtained, for example, by introducing mutation into the DNA encoding the original amino acid sequence as set forth in SEQ ID No: 1 or 3 using a conventional method such as site-specific mutagenesis, PCR and the like.

Furthermore, once the amino acid sequence of the desired enzyme has been determined, an appropriate nucleotide sequence encoding it can be determined, and the DNA can be chemically synthesized in accordance with a conventional method of DNA synthesis.

The present invention further provides the expression vectors comprising DNA such as the one mentioned above, the hosts transformed by said expression vectors, and a method for producing the enzymes or peptides of the present invention using these hosts.

Expression vectors contain an origin of replication, expression regulatory sequences etc., and they may differ with the hosts. As the hosts, there are mentioned procaryotes, for example, bacteria such as *Escherichia coli*, bacteria of genus Bacillus such as *Bacillus subtilis*, and eukaryotic microorganisms, for example, fungi such as yeast, for example the genus Saccharomyces such as *Saccharomyces cerevisiae*, and the genus Pichia such as *Pichia pastoris*, mold fungi of the genus Aspergillus such as *Aspergillus niger*, animal cells, for example the cultured cells of the silkworm, cultured cells of higher animals such as CHO cells and the like. Furthermore, plants may also be used as the host.

As set forth in Examples, in accordance with the present invention, by cultivating the host transformed by the DNA of the present invention, long chain-prenyl diphosphates may be accumulated in the culture medium, which may be harvested to produce long chain-prenyl diphosphates. Furthermore, in accordance with the invention, long chain-prenyl diphosphates may also be produced by contacting the mutant prenyl diphosphate synthase produced by the process of the invention to the substrate isopentenyl diphosphate and each allylic substrate such as dimethylallyl diphosphate and geranyl diphosphate.

When *Escherichia coli* is used as the host, for example, it is known that the host has the regulatory functions of the gene at the stage of transcribing mRNA from DNA and of translating protein from mRNA. As the promoter sequence regulating mRNA synthesis, in addition to the naturally occurring sequences (for example, lac, trp, bla, lpp, $P_L$, $P_R$, ter, T7, T3, etc.), there are known their mutants (for example, lac UV5) and the sequences (such as tac, trc, etc.) in which a naturally occurring promoter is artificially fused, and they can be used for the present invention.

It is known that the distance between the sequence of the ribosome binding site (GGAGG and similar sequences thereof) and the initiation codon ATG is important as the sequence that regulates the ability of synthesizing protein from mRNA. It is also well known that a terminator (for example, a vector containing rrn $PT_1$ $T_2$ is commercially available from Pharmacia) that directs transcription termination at the 3'-end affects the efficiency of protein synthesis by a recombinant.

As the vectors that can be used for preparation of the recombinant vectors of the present invention, commercially available vectors are used as they are, or various vectors may be mentioned that are induced depending on the intended use. For example, there may be mentioned pBR322, pBR327, pKK223-3, pKK233-2, pTrc99 and the like that have a replicon derived from pMB1; pUC18, pUC19, pUC118, pUC119, pTV118N, pTV119N, pBluescript, pHSG298, pHSG396 and the like that have been altered to enhance copy numbers; or pACYC177, pACYC184 and the like that have a replicon derived from p15A; and, furthermore, plasmids derived from pSC101, ColE1, R1, F factor and the like. Furthermore, fusion protein-expressing vectors that enable easier purification such as pGEX-2T, pGEX-3X, and pMal-c2 may be used. One example of the gene used as the starting material of the present invention has been described in Japanese patent application No. 6(1994)-315572.

Furthermore, in addition to plasmids, virus vectors such as λ phage or M13 phage, or transposon may be used for introduction of genes. With regard to the introduction of the gene into microorganisms other than *Escherichia coli*, gene introduction into organisms of genus Bacillus by pUB110 (commercially available from Sigma) or pHY300PLK (commercially available from Takara Shuzo) is known. These vectors are described in "Molecular Cloning" (J. Sambrook, E. F. Fritsch, and T. Maniatis, Cold Spring Harbor Laboratory Press) and "Cloning Vector" (P. H. Pouwels, B. B. Bnger, Valk, and W. J. Brammar, Elsevier), and catalogues of the manufacturers.

Integration of the DNA fragment encoding prenyl diphosphate synthase and, where needed, the DNA fragment having the function of regulating expression of the gene of said enzyme into these vectors can be performed by a known method using an appropriate restriction enzyme and ligase. Specific examples of the plasmids thus constructed include, for example, pBs-SacGGPS.

The microorganisms into which genes can be directly introduced using such recombinant vectors include *Escherichia coli* and microorganisms of the genus Bacillus. Such transformation can also be carried out using conventional methods, such as the $CaCl_2$ method and the protoplast method, that are described in "Molecular Cloning" (J. Sambrook, E. F. Fritsch, and T. Maniatis, Cold Spring Harbor Laboratory Press) and "DNA Cloning" Vol. I to III (D. M. Clover ed., IRL PRESS) etc.

In order to produce the mutant enzyme of the present invention, a host transformed as above is cultured, and then said culture is subjected to any conventional method comprising salting out, precipitation with an organic solvent, gel filtration, affinity chromatography, hydrophobic interaction chromatography, ion exchange chromatography and the like to recover and purify said enzyme.

The present invention provides a method for producing prenyl diphosphates having not less than 20 carbons such as geranylgeranyl diphosphate, geranylfarnesyl diphosphate, hexaprenyl diphosphate, heptaprenyl diphosphate, octaprenyl diphosphate, nonaprenyl diphosphate, decaprenyl diphosphate, undecaprenyl diphosphate, dodecaprenyl diphosphate, tridecaprenyl diphosphate, tetradecaprenyl diphosphate, pentadecaprenyl diphosphate, hexadecaprenyl diphosphate and the like using the enzyme of the present invention. In this method, the enzyme of the present invention is reacted in a medium, specifically an aqueous medium, and then, as desired, the desired prenyl diphosphates are harvested from the reaction medium.

As the enzyme, not only a purified enzyme but also a crude enzyme that may be semi-purified to various stages, or enzyme-containing products such as a mixture of the cultured mass of a microorganism or cultured substances may be used. Alternatively there may be used immobilized enzymes prepared according to the conventional method from said enzyme, said crude enzyme, or an enzyme-containing products.

As the substrate, there may be used dimethyl allyl diphosphates or geranyl diphosphate, farnesyl diphosphate or geranylgeranyl diphosphate, and isopentenyl diphosphates. As the reaction medium, water or an aqueous buffer solution, for example Tris buffer or phosphate buffer and the like, may be used.

By using the method of producing the mutant prenyl diphosphate synthase obtained by the present invention, the mutant prenyl diphosphate synthase derived from an archaea may be created that is more stable and that produces prenyl diphosphate having not less than 20 carbons such as geranylgeranyl diphosphate, geranylfarnesyl diphosphate, hexaprenyl diphosphate, heptaprenyl diphosphate, octaprenyl diphosphate, nonaprenyl diphosphate, decaprenyl diphosphate, undecaprenyl diphosphate, dodecaprenyl diphosphate, tridecaprenyl diphosphate, tetradecaprenyl diphosphate, pentadecaprenyl diphosphate, hexadecaprenyl diphosphate and the like.

In the claims and the specification of the present invention, amino acid residues are expressed by the one-letter codes or three-letter codes as described hereinbelow:

A; Ala; alanine
C; Cys; cysteine
D; Asp; aspartic acid
E; Glu; glutamic acid
F; Phe; phenylalanine
G; Gly; glycine
H; His; histidine
I; Ile; isoleucine
K; Lys; lysine
L; Leu; leucine
M; Met; methionine
N; Asn; asparagine
P; Pro; proline
Q; Gln; glutamine
R; Arg; arginine
S; Ser; serine
T; Thr; threonine
V; Val; valine
W; Trp; tryptophan
Y; Tyr; tyrosine Substitution of amino acid is expressed in the order of "the amino acid residue before substitution", "the number of the position of the amino acid residue," and "the amino acid residue after substitution," by the one-letter codes of amino acids. For example, the mutation wherein a Tyr residue at position 81 is substituted with a Met residue is expressed as Y81M. Furthermore, the deletion of an amino acid residue is expressed by "the amino acid residue before deletion", "the number of the position of the amino acid residue", and "–." For example, the deletion of Tyr at position 81 is expressed as Y81–.

EXAMPLES

The present invention is now explained with reference to specific examples, but they must not be construed to limit the invention in any way.

Example 1
Construction of a Plasmid Containing the Gene of Geranylgeranyl Diphosphate Synthase The gene of the geranylgeranyl diphosphate synthase (hereinafter referred to as SacGGPS) derived from *Sulfolobus acidocaldarius* was subcloned at the HindIII site of the plasmid vector pBluescript II (KS+) commercially available from Toyobo Co. LTD. The plasmid DNA was designated as pBs-SacGGPS. The SacGGPS gene is available from *Escherichia coli* pGGPS1/DH5α that was internationally deposited on Jan. 31, 1994, with the National Institute of Bioscience and Human Technology, Agency of Industrial Science and Technology, at Ibaraki, Japan under the accession number of FERM BP-4982.

Also, the entire nucleotide sequence of the SacGGPS gene has been published in Japanese patent application No. 6(1994)-315572, Shin-ichi Ohnuma et al. (1994), The Journal of Biological Chemistry Vol. 269:14792–14797, or a genetic information data bank such as GenBank under the accession number D28748. Since *Sulfolobus acidocaldarius* is also available from various depositories of microorganisms such as ATCC etc. (as ATCC No. 33909), the DNA of the gene region of SacGGPS can be obtained by the conventional gene cloning method.

Example 2
Synthesis of the Oligonucleotides for Introducing Mutation

Introduction of mutation of the geranylgeranyl diphosphate synthase was performed by, firstly, introducing mutation by the methods as described in Example 3 using a plasmid that has integrated thereinto the mutant geranylgeranyl diphosphate synthase (F77S) gene in which Phe at position 77 has been substituted by Ser in the mutant SacGGPS obtained in accordance with Example 2 in the specification of Japanese Patent Application No. 7(1995)-247043. This mutant geranylgeranyl diphosphate synthase gene was constructed by a chemical mutagen treatment, but other methods such as Kunkel method or PCR method may be used to construct the gene.

For introducing the desired mutation, the following oligonucleotides were designed and synthesized.

Primer DNA 1 (L74G, F77S): 5' GGTGCAGCAAT-TGAAGTTGGTCATACT 3' (SEQ ID No: 5)

For introducing mutation by the method as described in Example 3 using the gene in which mutation has been introduced by primer DNA 1, the following oligonucleotides were designed and synthesized.

Primer DNA 2 (L74G, F77A): 5' CATACTGCTACGCT-TGTTCATGATG 3' (SEQ ID No: 6)

Primer DNA 3 (L74G, F77G): 5' CATACTGGTACGCT-TGTTCATGATG 3' (SEQ ID No: 7).

These are designed for the purpose not only of introducing mutation into the codon encoding Leu at position 74 and Phe at position 77 of SacGGPS but also of newly introducing the cleavage site of the restriction enzyme BspHI or that of MunI.

The introduction of the BspHI cleavage site does not alter the amino acid sequence encoded by the SacGGPS gene due to codon degeneracy. This is intended for detecting the plasmid having an introduced mutation therein by agarose gel electrophoresis after digestion with BspHI or MunI, because a BspHI cleavage site or a MunI cleavage site is introduced simultaneously with the introduction of substitution-mutation into the codons corresponding to the amino acid residue at position 74 and the amino acid residue at position 77.

These primer DNA's were subjected to phosphorylation treatment at 37° C. for 30 minutes in the reaction solution shown below followed by denaturation at 70° C. for 10 minutes:

| | |
|---|---|
| 10 pmol/μl primer DNA | 2 μl |
| 10 × kination buffer | 1 μl |
| 10 mM ATP | 1 μl |
| H₂O | 5 μl |
| T4 Polynucleotide kinase | 1 μl | wherein the 10× kination buffer is 1000 mM Tris-Cl (pH 8.0), 100 mM $MgCl_2$, and 70 mM DTT.

Example 3
The Introduction of Substitution-mutation of the SacGGPS Gene

Using each primer DNA constructed in Example 2, substitution-mutation was introduced into the plasmid in accordance with the Kunkel method in which the mutant SacGGPS gene had been introduced. A Mutan-K kit commercially available from Takara Shuzo was used to perform the Kunkel method. The experimental procedure was as described in the kit insert. The substitution-mutation of the plasmid need not be conducted by the Kunkel method. For example, an identical result can be obtained by a method using the polymerase chain reaction (PCR).

Using *Escherichia coli* CJ236 in the Mutan-K kit as the host cell, a single strand DNA was prepared in which a thymine base in the plasmid pBs-SacGGPS is replaced with a deoxyuracil base.

The single strand DNA thus obtained is used as the template in the reaction in which a primer DNA for synthesizing a complementary strand is treated in the following reaction solution at 65° C. for 15 minutes and then annealed by allowing to stand at 37° C. for 15 minutes:

| | |
|---|---|
| Single strand DNA | 0.6 pmol |
| Annealing buffer | 1 μl |
| Primer DNA solution (Example 2) | 1 μl |
| H₂O make to a final volume of | 10 μl | wherein the annealing buffer solution is 200 mM Tris-Cl (pH 8.0), 100 mM $MgCl_2$, 500 mM NaCl, and 10 mM DTT.

Furthermore, 25 μl of the extension buffer solution, 60 units of *Escherichia coli* DNA ligase, and 1 unit of T4 DNA polymerase are added to synthesize the complementary strands at 25° C. for 2 hours. The extension buffer solution is 50 mM Tris-Cl (pH 8.0), 60 mM ammonium acetate, 5 mM $MgCl_2$, 5 mM DTT, 1 mM NAD, and 0.5 mM dNTP.

After the reaction is over, 3 μl of 0.2 M EDTA (pH 8.0) is added thereto and is subjected to treatment at 65° C. for 5 minutes to stop the reaction.

Example 4
Construction of a Plasmid Having the Gene of Farnesyl Diphosphate Synthase The gene of farnesyl diphosphate synthase derived from *Bacillus stearothermophilus* (referred to hereinafter as BstFPS) was subcloned into the KpnI and PstI sites of the plasmid vector pUC119. This plasmid DNA was designated as pEX1. The BstFPS gene is available from *Escherichia coli* JM109 (pEX1) that was internationally deposited on Sep. 26, 1991, with the National Institute of Bioscience and Human-Technology, Agency of Industrial Science and Technology, at Ibaraki, Japan under the accession number of FERM BP-3581.

Also, since the entire nucleotide sequence of the BstFPS gene has been published in Japanese Unexamined Patent Publication No. 5(1993)-219961 or a genetic information data bank such as GenBank under the accession number D1329 and *Bacillus stearothermophilus* is also available from various depositories of microorganisms such as ATCC etc. as ATCC No. 10149, the DNA of the gene region of BstFPS can be obtained by the conventional gene cloning method. Furthermore, for the purpose of a large-scale production of farnesyl diphosphate synthase derived from *Bacillus stearothermophilus,* the BstFPS gene was integrated into the NcoI and HindIII sites of the expression vector pTrc99A commercially available from Pharmacia [T. Koyama et al. (1993) J. Biochem. 113: 355–363]. This plasmid was designated as pEX11.

Example 5

Synthesis of the Oligonucleotides for Introducing BstFPS Mutation and Introduction of Substitution-mutation The introduction of mutation into the BstFPS gene was conducted by the polymerase chain reaction (PCR) method using the expression vector pEX11 constructed in Example 4. In order to introduce mutation, the following oligonucleotides were designed and synthesized.

Primer DNA 4: 5' AAACAGACCATGGCGCTTTC 3' (SEQ ID No: 8)

Primer DNA 5: 5' CAGCCAAGCTTTTAATGGTC 3' (SEQ ID No: 9)

Primer DNA 6: 5' CTTTGATTCATGATGATTTG 3' (SEQ ID No: 10)

Primer DNA 7: 5' ATCATCATGAATCAAAGAAGACG-TATGGCCCATTTC 3' (SEQ ID No: 11)

Primer DNA 8: 5' ATCATCATGAATCAAAGAGGCCG-TATGGCCCATTTC 3' (SEQ ID No: 12)

Primer DNA 9: 5' ATCATCATGAATCAAAGAGCCCG-TATGGCCCATTTC 3' (SEQ ID No: 13)

Primer DNA 10: 5' ATGGACAACGATGATTTGCG 3' (SEQ ID No: 14)

Primer DNA 11: 5' CAAATCATCATGGATCAAAG 3' (SEQ ID No: 15)

The polymerase chain reaction was carried out using ExTaq commercially available from Takara Shuzo in accordance with the manufacturer's instructions. In order to introduce substitution-mutation, each of the combinations of primer DNA 4 and primer DNA 7, primer DNA 4 and primer DNA 8, primer DNA 4 and primer DNA 9, or primer DNA 5 and primer DNA 6 was employed to carry out the polymerase chain reaction.

The reaction cycle that comprised 30 seconds at 94° C., 30 seconds at 50° C., and one minute at 72° C. was repeated 35 times. The DNA fragments that resulted from the reaction were subjected to agarose gel electrophoresis, and then were purified by excising those DNA fragments that have the desired length.

The DNA fragment obtained from each of the combinations of primers by the polymerase chain reaction was each designated as fragment 1 (primer 4 and primer 7), fragment 2 (primer 4 and primer 8), fragment 3 (primer 4 and primer 9), and fragment 4 (primer 5 and primer 6).

Furthermore, fragments 1, 2 and 3 were cleaved with the restriction enzyme NcoI and the restriction enzyme BspHI, and fragment 4 was cleaved with the restriction enzyme HindIII and the restriction enzyme BspHI to adjust the ends of the fragments, and then fragment 1 and fragment 4, fragment 2 and fragment 4, and fragment 3 and fragment 4 were subjected to ligation. For the ligation, the ligation kit commercially available from Takara Shuzo was employed. Each of the ligated fragments was integrated into the NcoI and HindIII sites of plasmid vector pTrc99A. Though the substitution-mutated pEX11 may be cleaved with the restriction enzyme BspHI at the BstFPS coding region, the amino acid at this site is not replaced due to degeneracy of genetic codes. The resultant DNAs were induced into the host cells by the method shown in Example 6.

The relationship between each fragment and the mutant is shown below:

Fragment 1 and fragment 4→I78G, Y81S

Fragment 2 and fragment 4→I78G, Y81A

Fragment 3 and fragment 4→I78G, Y81G

For each substitution-mutation, pEX11, primer DNA 10 and primer DNA 11 were further used to conduct a polymerase chain reaction. The reaction cycle that comprised 30 seconds at 94° C., 15 seconds at 54° C., and four minutes at 72° C. was repeated 30 times. Then the DNA fragments having the desired lengths were purified by agarose gel electrophoresis, and the ends of the DNA fragments were adjusted using the Klenow fragment. They were then phosphorylated using T4 polynucleotide kinase and then were subjected to self-ligation. The Klenow fragment and T4 polynucleotide kinase commercially available from Takara Shuzo were used in accordance with the manufacturer's instructions.

The above-mentioned ligation kit was used for self-ligation. The relationship between each substitution-mutation pEX11 and deletion-mutation constructed by the polymerase chain reaction using primer DNA 10 and DNA 11 is shown below:

I78G, Y81S→I78G, Y81S, P89-, S90-

I78G, Y81A→I78G, Y81A, P89-, S90-

I78G, Y81G→I78G, Y81G, P89-, S90-

The deletion mutant pEX11 thus constructed is identical with substitution-mutant pEX11 except that the former has the cleavage site of the restriction enzyme BspHI which was formed at the time of introducing substitution-mutation, so that the deletion mutant pEX11 can be differentiated from the original substitution-mutant pEX11.

Example 6

Construction of a Transformant Introduced with Genes of Substitution-mutant SacGGPS and BstFPS The DNA solutions prepared in accordance with Example 3 and Example 5 were used to transform *Escherichia coli* XL1-Blue by the $CaCl_2$ method. An alternative method such as electroporation gives a similar result. A host cell other than *Escherichia coli* XL1-Blue also gives a similar result.

The transformant, for example JM109 and so on, obtained by the $CaCl_2$ method was inoculated onto the agar plate containing ampicillin, a selectable marker of transformants, and was incubated overnight at 37° C.

Of the transformants obtained as above, the substitution mutant pBs-SacGGPS plasmid or mutant pEX11 plasmid that has a cleavage site of BspHI or MunI on the SacGGPS coding region or BstFPS coding region was selected. As the mutant pEX11 plasmid in which deletion-mutation was introduced, the mutant pEX11 plasmid that does not have the BspHI cleavage site at the BstFPS coding region was selected.

The nucleotide sequence in the neighborhood of the codon corresponding to the amino acid residue that undergoes mutation of the SacGGPS gene of the selected substitution mutant pBs-SacGGPS plasmid or of the BstFPS gene of the mutant pEX11 plasmid was determined by the dideoxy method thereby confirming the introduction of the desired mutation.

Example 7
Measurement of Activity of the Mutant Prenyl Diphosphate Synthase Crude enzyme solutions were prepared as follows from a total of 11 transformants comprising 9 mutant SacGGPS genes, one wild type SacGGPS gene, and one wild type BstFPS gene that were obtained in Example 6.

The transformants cultured overnight in the 2×LB medium were centrifuged to harvest cells, and then the cells were suspended into the lysis buffer (50 mM Tris-Cl (pH 8.0), 10 mM β-mercaptoethanol, 1 mM EDTA). They were lysed by sonication and then centrifuged at 4° C. at 10,000 r.p.m. for 10 minutes. The supernatant obtained was treated at 55° C. for one hour to inactivate the activity of prenyl diphosphate synthase derived from *Escherichia coli*.

They were further centrifuged under the same condition and the supernatants obtained were used as a crude enzyme extract. The reaction was carried out at 55° C. for one hour in the following reaction solution:

| | |
|---|---|
| [1-$^{14}$C]-isopentenyl diphosphate (1 Ci/mol) | 25 nmol |
| Allylic diphosphate (geranyl diphosphate) | 25 nmol |
| Potassium phosphate buffer (pH 5.8) | 50 mM |
| MgCl$_2$ | 5 mM |
| Enzyme solution | 100 μg |
| H$_2$O to make | 200 μl |

After the reaction, 200 μl of saturated NaCl solution was added to the reaction solution and one ml of water-saturated butanol was added thereto, which was then agitated, centrifuged, and separated into two phases. To 800 μl of the butanol layer obtained was added 3 ml of a liquid scintillator and then the radioactivity was measured by the liquid scintillation counter. The remainder of the butanol layer was evaporated by purging nitrogen gas thereinto while heating the layer in order to concentrate to a volume of about 0.5 ml. To the concentrate were added two ml of methanol and one ml of potato acid phosphatase solution (2 mg/ml potato acid phosphatase, 0.5 M sodium acetate (pH 4.7)) to effect the dephosphorylation reaction at 37° C.

Figure 2:
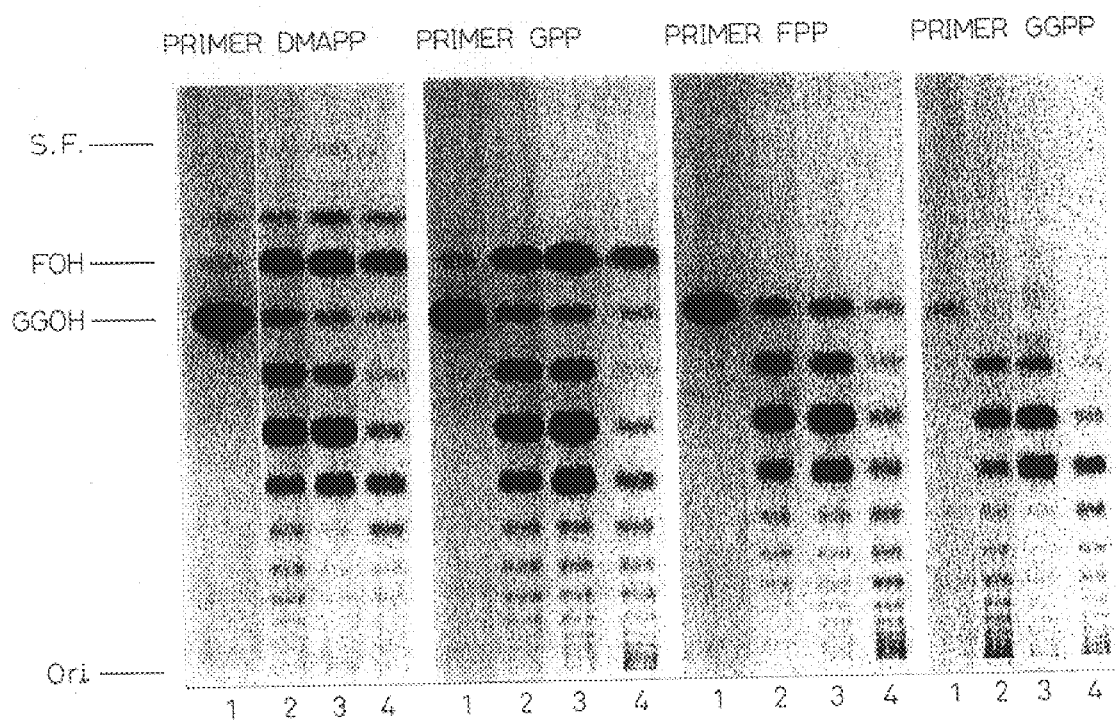
FIG. 2 shows a photograph of a profile of thin layer chromatography obtained on the dephosphorylated reaction products of the mutant SacGGPS synthase when dimethyl allyl diphosphate (DMAPP), geranyl diphosphate (GPP), farnesyl diphosphate (FPP), and geranylgeranyl diphosphate (GGPP) were each used as the allylic substrate. In the figure, Ori. represents the origin of development, and S.F. represents the solvent front. Lane 1 shows a result for the wild type SacGGPS; lane 2, for the mutant SacGGPS (L74G, F77S); lane 3, for the mutant SacGGPS (L74G, F77A), and; lane 4, for the mutant SacGGPS (L74G, F77G).

Subsequently the dephosphorylated reaction product was extracted with 3 ml of n-pentane. This was concentrated by evaporating the solvent by purging nitrogen gas thereinto, which was then analyzed by TLC (reverse phase TLC plate: LKC18 (Whatman), development solvent: acetone/water=9/1 or acetone/water=19/1). The dephosphorylated reaction product that was developed was analyzed by the Bio Image Analyzer BAS2000 (Fuji Photo Film) to determine the location of radioactivity. The result of the mutant prenyl diphosphate synthase at whose gene mutation has been introduced is shown in FIG. 2. The result of the two mutant prenyl diphosphate synthases at whose gene mutation has been introduced is shown in FIG. 3. The result regarding the other mutant prenyl diphosphate synthases in which mutation has been introduced with the BstFPS gene was the same as in FIG. 3.

Reference to Deposition of Microorganisms
Name of International Depository Authority:
National Institute of Bioscience and Human Technology, Agency of Industrial Science and Technology
Address: 1–3, Higashi 1-chome, Tsukuba-shi, Ibaraki 305 Japan
(1) *Escherichia coli* pGGPS1/DH5α
   Deposition No.: FERM BP-4982
   Deposition date: Jan. 31, 1994
(2) *Escherichia coli* JM109 (pEX1)
   Deposition No.: FERM BP-3581
   Deposition Date: Sep. 26, 1991

---

What is claimed is:

1. A mutant prenyl diphosphate synthase having a modified amino acid sequence, wherein both an amino acid located at the fifth position upstream of $D_1$ of the Asp-rich domain $D_1D_2X_1(X_2X_3)X_4D_3$ of conserved region II of prenyl diphosphate synthase and an amino acid located at the eighth position upstream of $D_1$ of the Asp-rich domain $D_1D_2X_1(X_2X_3)X_4D_3$ of conserved region II of prenyl diphosphate synthase have each been substituted by another amino acid, wherein the mutant prenyl diphosphate synthase is capable of synthesizing a product having more than 30 carbon atoms.

2. An enzyme according to claim 1 wherein the reaction products of said prenyl diphosphate synthase are hexaprenyl diphosphate, heptaprenyl diphosphate, octaprenyl diphosphate, nonaprenyl diphosphate, decaprenyl diphosphate, undecaprenyl diphosphate, dodecaprenyl diphosphate, tridecaprenyl diphosphate, tetradecaprenyl diphosphate, pentadecaprenyl diphosphate and hexadecaprenyl diphosphate.

3. An enzyme according to claim 1 wherein the prenyl diphosphate synthase is a homodimer.

4. An enzyme according to claim 1 wherein the prenyl diphosphate synthase is derived from archaea.

5. An enzyme according to claim 1 wherein the prenyl diphosphate synthase is derived from a bacterium.

6. An enzyme according to claim 1 wherein the prenyl diphosphate synthase is derived from *Sulfolobus acidocaldarius*.

7. An enzyme according to claim 1 wherein the prenyl diphosphate synthase is derived from *Bacillus stearothermophilus*.

8. An enzyme according to claim 1 wherein the prenyl diphosphate synthase maintains the properties of the corresponding native prenyl diphosphate synthase.

9. An enzyme according to claim 1 wherein the prenyl diphosphate synthase is a thermostable enzyme.

10. A mutant prenyl diphosphate synthase according to claim 1, wherein Leu at the position 74 and Phe at the position 77 of geranylgeranyl diphosphate synthase having the amino acid sequence as set forth in SEQ ID No: 1 have each been substituted by another amino acid.

11. A mutant prenyl diphosphate synthase according to claim 1, wherein Ile at the position 78 and Tyr at the position 81 of farnesyl diphosphate synthase having the amino acid sequence as set forth in SEQ ID No: 3 have each been substituted by another amino acid.

12. A mutant prenyl diphosphate synthase according to claim 1, wherein Ile at the position 78 and Tyr at the position 81 of farnesyl diphosphate synthase having the amino acid sequence as set forth in SEQ ID No: 3 have each been substituted by another amino acid and Pro at the position 89 and Ser at the position 90 of said farnesyl diphosphate synthase have been deleted.

13. A DNA encoding an enzyme according to claim 1.

14. An RNA transcribed from the DNA according to claim 13.

15. A recombinant vector comprising a DNA according to claim 13.

16. A host cell transformed with a recombinant vector according to claim 15.

17. A process for production of an enzyme according to claim 1, comprising the steps of culturing host cells transformed with an expression vector comprising a DNA coding for said enzyme, and harvesting the expressed enzyme from the culture.

18. A process for production of prenyl diphosphate having at least 30 carbons characterized in that an enzyme according to claim 1 or an enzyme produced by the method according to claim 17 is brought into contact with a substrate selected from the group consisting of isopentenyl diphosphate, dimethylallyl diphosphate, geranyl diphosphate, farnesyl diphosphate, and geranylgeranyl diphosphate.

19. An enzyme according to claim 1 wherein the enzyme is further modified by deletion of amino acid $X_2$ and/or amino acid $X_3$.

20. A mutant prenyl diphosphate synthase of claim 3, wherein the amino acid residue located at the fifth position upstream of $D_1$ of the Asp-rich domain $D_1D_2X_1(X_2X_3)X_4D_3$ of conserved region II is selected from the group consisting of Ala, Ser and Gly and the amino acid located at the eighth position upstream of $D_1$ of the Asp-rich domain $D_1D_2X_1(X_2X_3)X_4D_3$ of conserved region II is Gly.

* * * * *